US012582770B2

(12) United States Patent
Yang

(10) Patent No.: US 12,582,770 B2
(45) Date of Patent: Mar. 24, 2026

(54) DRIP MONITORING SYSTEM AND METHOD THEREOF

(71) Applicants: Mikotek Information Inc., Taipei City (TW); Ching-Wen Yang, Taipei City (TW)

(72) Inventor: Ching-Wen Yang, Taipei City (TW)

(73) Assignees: Mikotek Information Inc., Taipei City (TW); Ching-Wen Yang, Taipei City (TW)

( * ) Notice: Subject to any disclaimer, the term of this patent is extended or adjusted under 35 U.S.C. 154(b) by 728 days.

(21) Appl. No.: 17/457,431

(22) Filed: Dec. 2, 2021

(65) Prior Publication Data

US 2023/0088594 A1 Mar. 23, 2023

(30) Foreign Application Priority Data

Sep. 23, 2021 (TW) .................................. 110135310

(51) Int. Cl.
*A61M 5/168* (2006.01)
*A61M 5/14* (2006.01)
*G01G 23/01* (2006.01)

(52) U.S. Cl.
CPC ........ *A61M 5/1689* (2013.01); *A61M 5/1417* (2013.01); *G01G 23/01* (2013.01); *A61M 2205/18* (2013.01); *A61M 2205/3393* (2013.01); *A61M 2205/3584* (2013.01); *A61M 2205/502* (2013.01); *A61M 2205/60* (2013.01); *A61M 2205/702* (2013.01)

(58) Field of Classification Search
CPC .............. G01G 23/01; A61M 5/16845; A61M 5/16895; A61M 2205/3393
See application file for complete search history.

(56) References Cited

U.S. PATENT DOCUMENTS

| | | | |
|---|---|---|---|
| 4,757,867 A | 7/1988 | Rosenthal et al. | |
| 9,956,893 B2 | 5/2018 | Yang et al. | |
| 10,016,551 B2 | 7/2018 | Hersenius | |
| 2018/0140771 A1* | 5/2018 | Baek ................... | A61M 5/1415 |

FOREIGN PATENT DOCUMENTS

| TW | 201400844 A | 1/2014 |
|---|---|---|
| TW | M624327 U | 3/2022 |

* cited by examiner

*Primary Examiner* — Stephen D Meier
*Assistant Examiner* — Leo T Hinze
(74) *Attorney, Agent, or Firm* — CKC & Partners Co., LLC

(57) ABSTRACT

The drip monitoring system comprises a weighing device to weigh a carrying weight. The weighing device includes a gravity sensor to sense a motion data of the weighing device. The processing element gathers the carrying weight to compare with an empty weight. The processing element gathers the motion data of the weighing device when the carrying weight is less than the empty weight. The processing element determines whether the weighing device is in a calibration orientation or not according to the motion data. When the weighing device is in the calibration orientation, the processing element controls the weighing device to perform a return to zero calibration process.

18 Claims, 5 Drawing Sheets

300

400

500

DRIP MONITORING SYSTEM AND METHOD THEREOF

CROSS-REFERENCE TO RELATED APPLICATION

This application claims priority to Taiwan Application Serial Number 110135310, filed Sep. 23, 2021, which is herein incorporated by reference.

BACKGROUND OF THE INVENTION

Field of Invention

The present invention relates to a drip monitoring system and a method thereof, in particular to a drip monitoring system and a method capable of performing automatic calibration process.

Description of Related Art

Medical infusions are mostly gravity drips, that is, drip bags or drip bottles are hung on a fixed shelf, so that the drips drip into the blood due to natural gravity. At present, the monitoring method of the drip process can be carried out by using the drip weight weighing device to weigh the weight of the drip bag or the drip bottle to monitor whether the drip in the drip bag or the drip bottle is below the warning value to generate an alarm to notify the medical staff for help.

However, the long-term carrying of the drip bag or the drip bottle often causes deformation of the drip weight weighing device, which results in errors in the weighed weight of the drip bag or drip bottle to cause false alarms to notify the medical staff. Therefore, how to solve the problem of false alarms to notify the medical staff due to the deformation of the drip weight weighing device is an urgent issue in the industry.

SUMMARY

According to an aspect of the present invention, a drip monitoring system is provided. The drip monitoring system comprises a processing element, a weighing device configured to weigh a carrying weight, and an alarm element configured to generate an alarm message according to a control signal from the processing element. The weighing device includes a gravity sensor to sense a motion data of the weighing device. The processing element gathers the carrying weight to compare with an alarm weight. The processing element compares the carrying weight with an empty weight when the carrying weight is less than the alarm weight. The empty weight is less than the alarm weight. The processing element gathers the motion data of the weighing device when the carrying weight is less than the empty weight. The processing element determines whether the weighing device is in a calibration orientation or not according to the motion data. When the weighing device is in the calibration orientation, the processing element controls the weighing device to perform a return to zero calibration process.

In an embodiment, when the carrying weight is larger than the alarm weight, the processing element gathers the carrying weight to compare with the alarm weight again after an interval.

In an embodiment, the weighing device has a hook to hang a drip bag or a drip bottle, wherein the calibration orientation is the hook perpendicular to the ground.

In an embodiment, the drip monitoring system further comprises a communication element coupled to the processing element configured to transmit the alarm message to a user device.

In an embodiment, when the weighing device is not in the calibration orientation, the processing element prohibits the weighing device from performing the return to zero calibration process and transmit a calibration not being executed message to the user device through the communication element.

In an embodiment, the drip monitoring system further comprises a display to display the calibration not being executed message.

In an embodiment, the processing element gathers the motion data to calculate a change of the motion data in a time period.

In an embodiment, when the change of the motion data in the time period is larger than a threshold, the processing element controls the alarm element to generate the alarm message.

In an embodiment, when the change of the motion data in the time period is less than the threshold, the processing element transmits the motion data to a server, and the server determines a travel direction of the weighing device according to the motion data.

In an embodiment, the weighing device further comprises a positioning element configured to broadcast an identification code and the motion data through a wireless signal. A server determines a location of the weighing device according to the identification code and the motion data.

According to an aspect of the present invention, a drip monitoring method is provided. The drip monitoring method comprises measuring a carrying weight by a weighing device, gathering the carrying weight to compare with an alarm weigh by a processing element, comparing the carrying weight with an empty weight by the processing element when the carrying weight is less than the alarm weight, wherein the empty weight is less than the alarm weight, gathering the motion data of the weighing device by the processing element when the carrying weight is less than the empty weight, determining whether the weighing device is in a calibration orientation by the processing element according to the motion data, and controlling the weighing device to perform a return to zero calibration process by the processing element when the weighing device is in the calibration orientation. The weighing device includes a gravity sensor to sense a motion data of the weighing device.

In an embodiment, when the carrying weight is larger than the alarm weight, the processing element gathers the carrying weight to compare with the alarm weight again after an interval.

In an embodiment, the weighing device has a hook to hang a drip bag or a drip bottle, wherein the calibration orientation is the hook perpendicular to the ground.

In an embodiment, the drip monitoring method further comprises to transmit an alarm message to a user device through a communication element.

In an embodiment, when the weighing device is not in the calibration orientation, the processing element prohibits the weighing device from performing the return to zero calibration process and transmit a calibration not being executed message to the user device through the communication element.

In an embodiment, the drip monitoring method further comprises to display the calibration not being executed message in a display.

In an embodiment, the processing element gathers the motion data to calculate a change of the motion data in a time period.

In an embodiment, when the change of the motion data in the time period is larger than a threshold, the processing element controls the alarm element to generate an alarm message.

In an embodiment, when the change of the motion data in the time period is less than the threshold, the processing element transmits the motion data to a server, and the server determines a travel direction of the weighing device according to the motion data.

In an embodiment, the weighing device further comprises a positioning element configured to broadcast an identification code and the motion data through a wireless signal, wherein a server determine a location of the weighing device according to the identification code and the motion data.

Accordingly, a gravity sensor is installed on the weighing device to sense the motion data of the weighing device. The motion data is used to determine the current orientation of the weighing device. The current orientation is used to determine whether to perform a return to zero calibration process. Accordingly, the shortcomings of performing the return to zero calibration process by the weighing device in an abnormal orientation are eliminated. Furthermore, it is possible to locate and determine whether an unexpected situation has occurred based on the real-time motion data and the amount of change.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

In order to make the above and other objects, features and advantages of the disclosure more comprehensible, several embodiments accompanied with figures are described in detail below.

DETAILED DESCRIPTION

Figure 1:
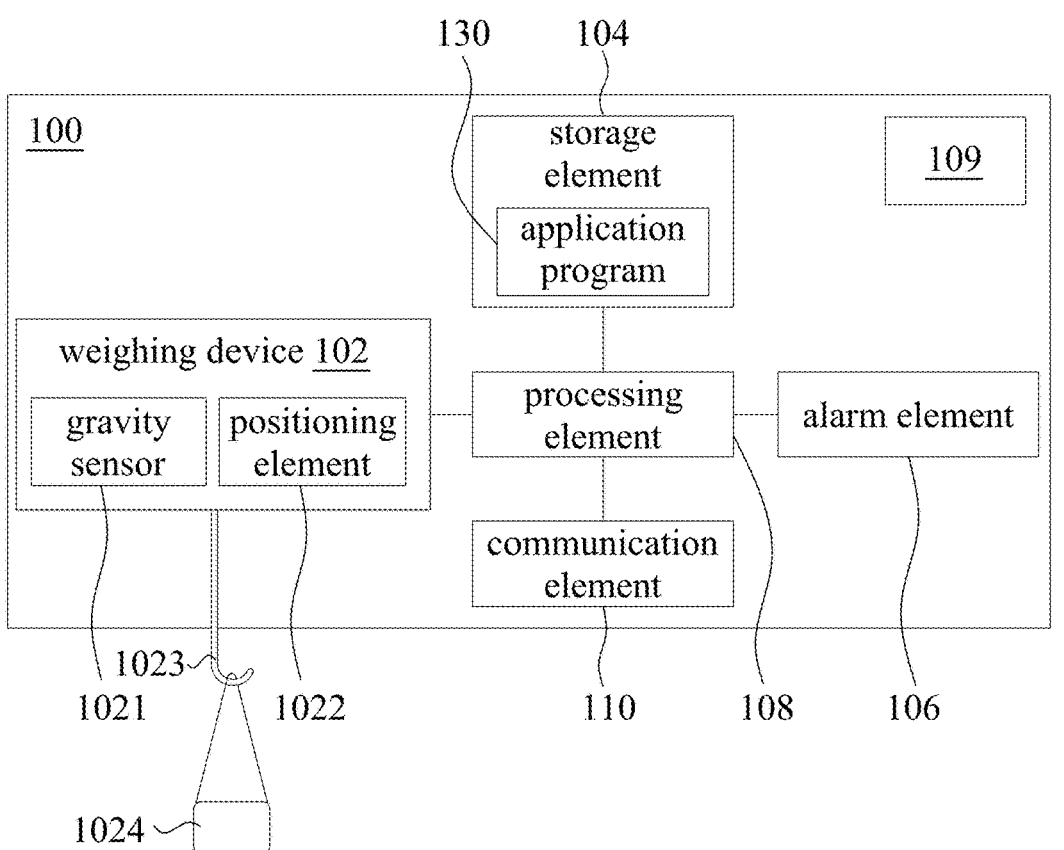
FIG. 1 shows a block diagram of a drip monitoring system capable of automatic calibration according to an embodiment.

Reference will now be made in detail to the present preferred embodiments of the disclosure, examples of which are illustrated in the accompanying drawings. Wherever possible, the same reference numbers are used in the drawings and the description to refer to the same or like parts.

To comprehensively describe the disclosure in detail, reference may be made to the accompanying drawings and various embodiments. Meanwhile, components and steps known by the public are not described in the embodiments to prevent unnecessary limitations from being imposed to the disclosure.

Terms such as "couple" or "connect" used in the embodiments may refer to two or more components being in physical or electrical contact with each other "directly", two or more components being in physical or electrical contact with each other "indirectly", or acting of two or more components with each other.

The foregoing and other technical content, features, and effects of the present invention can be clearly presented below in detailed descriptions of embodiments with reference to the drawings.

FIG. 1 shows a block diagram of a drip monitoring system capable of automatic calibration according to an embodiment. The drip monitoring system 100 includes a weighing device 102, a storage element 104, an alarm element 106, a processing element 108 and a communication element 110. The processing element 108 is electrically coupled to the weighing device 102, the storage element 104, the alarm element 106 and the communication element 110. In one embodiment, the drip monitoring system 100 can connect to an Internet through the communication component 110 to communicate with a remote medical care platform or a hand-held device of a medical staff. The drip monitoring system 100 transmits the real-time monitoring value detected by the drip monitoring system 100 to the remote medical care platform or a hand-held device of a medical staff. In an embodiment, the hand-held device of a medical staff is a portable electronic device, such as a tablet, a smart phones, a palmtop computer, or a personal digital assistants. The processing element 108 is a central processing unit (CPU) or other programmable microprocessors. In an embodiment, the processing element 108, the weighing device 102, the storage element 104, the alarm element 106 and the communication element 110 are arranged in a box to form the drip monitoring system 100.

The weighing device 102 is configured to weigh the weight of an object to be weighed. The object to be weighed may be, but not limited to, a drip bag or a drip bottle. The processing element 108 can perform subsequent processing according to the weight weighed by the weighing device 102. The storage element 104 may include various types of storage units, such as, but not limited to a register, a flash memory, or a combination thereof. The storage element 104 is configured to store data. In one embodiment, the storage element 104 is configured to store an application program 130. The processing element 108 accesses the storage element 104 to execute the application program 130 to process the weight weighed by the weighing device 102. The alarm element 106 may include, but is not limited to, a buzzer, a light emitting element, or a combination thereof. The alarm element 106 generates an alarm message according to the control of the processing element 108 to notify the medical staff through the communication element 110. The alarm message is sound, flash, or a combination thereof.

Figure 6:
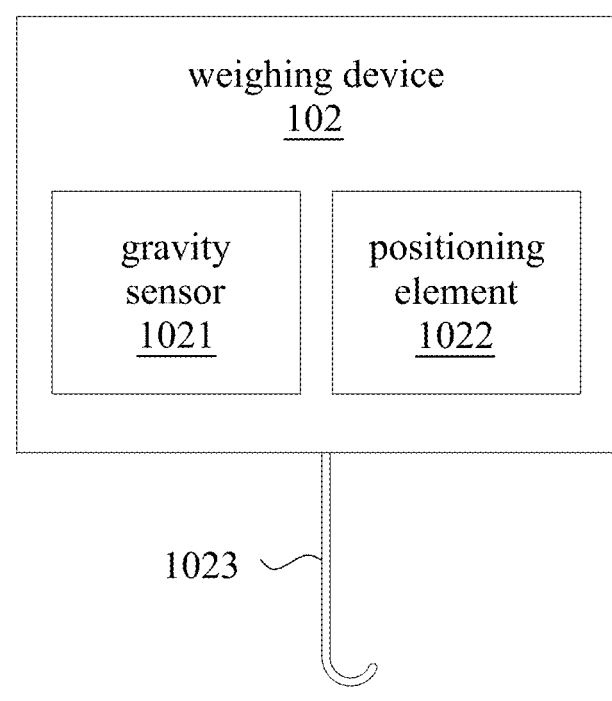
FIG. 6 illustrates the weighing device in a calibration orientation.
Figure 7:
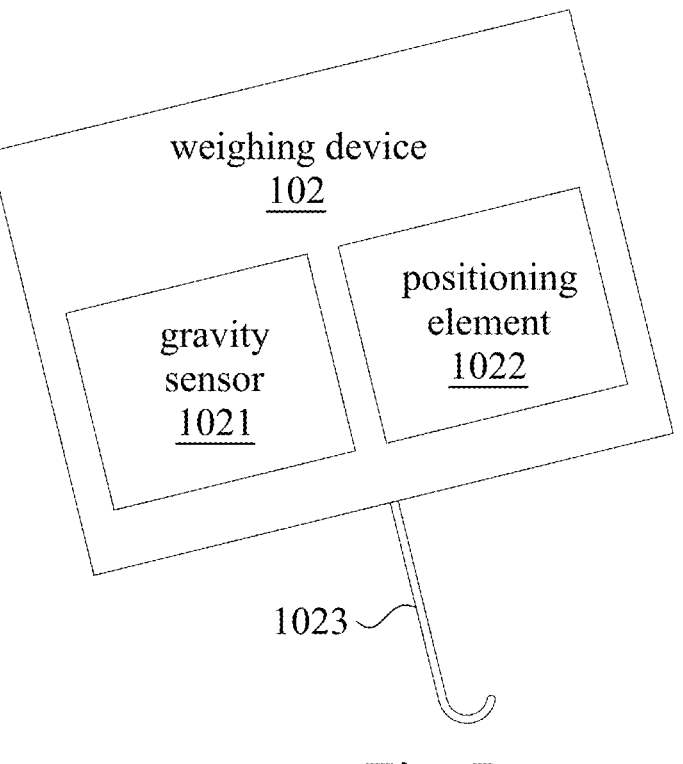
FIG. 7 illustrates the weighing device in a slanted state.

In one embodiment, the weighing device 102 further includes a gravity sensor (G-sensor) 1021 for sensing the motion data of the weighing device 102. FIG. 7 illustrates the weighing device 102 in a slanted state. In one embodiment, when the weighing device 102 is in a slanted state as shown in FIG. 7 or lying state, or when the weighing device 102 is in a moving or shaking state, these situations cause the calibration weight is inaccurate, which may fail the calibration process. Therefore, for preventing the weighing device 102 from performing calibration in an abnormal state, the gravity sensor 1021 is used to determine whether the motion data of the weighing device 102 is in the set calibration orientation or not before the weighing device 102 performing the calibration. FIG. 6 illustrates the weighing device 102 in a calibration orientation. In one embodiment, the set calibration orientation is the orientation of the hook 1023 of the weighing device 102 used to hang the drip bag 1024 (or drip bottle) perpendicular to the ground. Accordingly, when the weighing device 102 is performing calibration, the processing element 108 first reads the motion data value detected by the gravity sensor 1021, and determines whether the motion data value is within the set calibration orientation or not. If the motion data value is within the set calibration orientation, the processing element 108 performs a return to zero calibration process on the weighing device 102. In contrast, if the motion data value is not within the set calibration orientation, that is, the hook 1023 is not perpendicular to the ground, the processing element 108 prohibits the weighing device 102 from performing a return to zero calibration process and informs relevant personnel for processing.

In an embodiment, the gravity sensor 1021 is an accelerometer (G-Sensor), a magnetometer (M-Sensor), a gyroscope (Gyroscope), a gravity-vibration sensor (GV-Sensor), a linear acceleration sensor (LA-Sensor), a rotation vector sensor (RV-Sensor), a tilt sensor (Tilt-Sensor) or an assembly of the above devices. In an embodiment, the gravity sensor 1021 directly provides three-axis sensing signals, which are X-axis acceleration (velocity) parameters, Y-axis acceleration (velocity) parameters, and Z-axis acceleration (velocity) parameters. In this embodiment, a three-axis inertial sensor is used for detecting. In another preferred embodiment, a six-axis inertial sensor is used for detecting, in which three-axis acceleration is used for detection, and the other three-axis angular acceleration is used for verification to increase the reliability of the detection result. It is noticed that nine-axis acceleration, nine or more axis acceleration, or other similar means also can be used in the present application to detect motion data.

Figure 2:
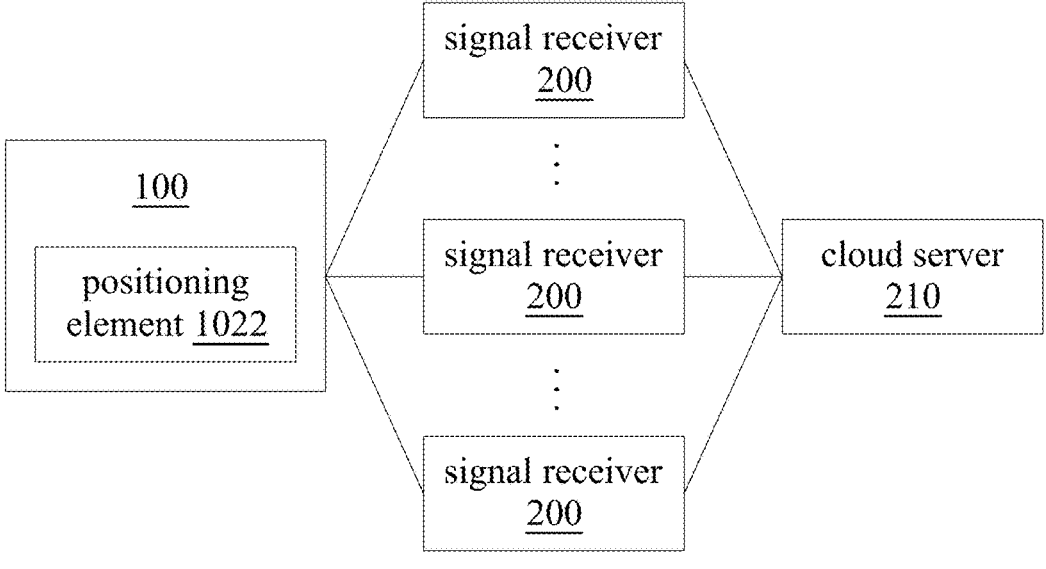
FIG. 2 is a diagram of a positioning system according to an embodiment of the present application.

In another embodiment, when the patient is moved, the drip monitoring system 100 hanging a drip bag 1024 (or drip bottle) is moved together for preventing the patient in the infusion be interrupted. Therefore, the weighing device 102 further includes a positioning element 1022 to detect the moving position of the patient in a medical institution. FIG. 2 is a diagram of a positioning system according to an embodiment of the present application, which is used to position the drip monitoring system 100 in a medical institution. In one embodiment, the positioning element 1022 is a Wi-Fi, Bluetooth, Ultra-wideband (UWB) or ZigBee signal transmission element. In a preferred embodiment, if the positioning element 1022 is a Bluetooth signal transmission element, a plurality of signal receivers 200, such as Bluetooth signal receivers, are arranged in different locations in a medical institution for positioning. The positioning element 1022 of each drip monitoring system 100 has its own identification code. The positioning element 1022 can periodically use a signal, such as a Bluetooth signal, to broadcast its identification code. Accordingly, the signal receiver 200 within the communication range can detect the presence of the positioning element 1022. The signal receiver 200 can detect and receive signals from the positioning element 1022, such as Bluetooth signals, within its effective communication range. When one of the signal receivers 200 detects the Bluetooth signal of the positioning element 1022 and receives the identification code in the Bluetooth signal, the signal receiver 200 will report the identification code to the cloud server 210. When the cloud server 210 receives the identification code, the cloud server 210 can determine the positioning element 1022 of the drip monitoring system 100 based on the identification code and determine the position of the drip monitoring system 100 in this medical institution based on the location of the signal receiver 200 that reports the identification code to the cloud server 210. It is noticed that the above positioning method is only an embodiment and is not used to limit the implementation of this present application. Other positioning methods can also be used in this present application to locate the drip monitoring system 100. In an embodiment, the cloud server 210 may be a medical care platform of a medical institution.

In another embodiment, because the weighing device 102 of this application further includes a gravity sensor 1021, the positioning element 1022 can use the Bluetooth signal to broadcast not only its own identification code but also the real-time motion data detected by the gravity sensor 1021. The gravity sensor 1021 can sense the motion data, such as the acceleration, the angular acceleration, the direction, and the movement amount, of the drip bag 1024 (or the drip bottle). The motion data is used to identify the real-time use status of the drip bag 1024 (or drip bottle), and to indirectly determine whether the patient's posture is likely to fall or not. In one embodiment, when the drip bag 1024 (or drip bottle) is used to provide fluid to the patient, the drip bag 1024 (or drip bottle) should be perpendicular to the ground. Therefore, when the patient has an abnormal pulling condition during the drip bag 1024 (or drip bottle) providing fluid to the patient or the angle for providing fluid to the patient is incorrect, it is dangerous for the dripping. Therefore, this present application uses the positioning element 1022 to broadcast the real-time motion data detected by the gravity sensor 1021. When one of the signal receivers, such as the signal receiver 200, detects the Bluetooth signal of the positioning element 1022, the signal receiver 200 may transfer not only the identification code but also the motion data to the cloud server 210. The cloud server 210 can determine whether the drip bag 1024 (or drip bottle) of a corresponding drip monitoring system 100 is in an abnormal use state or not based on the identification code and the motion data. In one embodiment, when the patient is carrying the drip bag or drip bottle to move, once a falling down event happens, the drip bag 1024 (or drip bottle) may fall. Therefore, the real-time motion data detected by the gravity sensor 1021 shows the drip bag 1024 (or drip bottle) is falling, which can be used to indirectly determine whether a falling down event has occurred for the patient and to notify the medical staff for help. In one embodiment, the change state of the motion data in a short time interval, such as a time interval of 2-3 seconds, is used to determine whether the drip bag 1024 (or the drip bottle) is in an abnormal use state. It is noticed that other determining methods can also be used in this present application.

Figure 3:
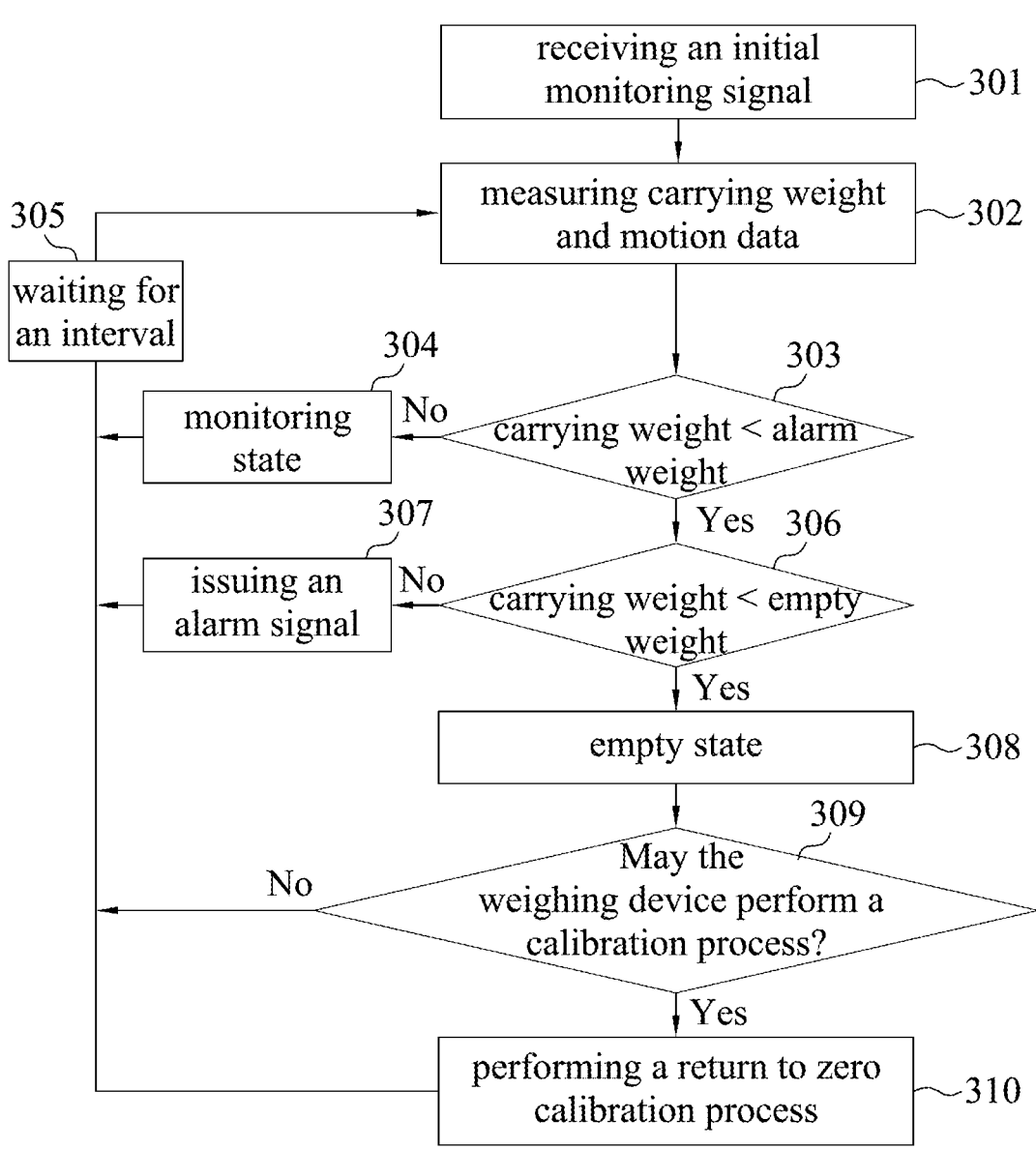
FIG. 3 shows a drip monitoring method capable of performing automatic calibration according to an embodiment of the present application.

FIG. 3 shows a drip monitoring method capable of performing automatic calibration according to an embodiment of the present application. Please refer to FIG. 1 and FIG. 3. The drip monitoring method 300 capable of performing automatic calibration can be applied to the drip monitoring system 100 of FIG. 1. The processing element 108 accesses the application program 130 in the storage element 104 to perform the drip monitoring method 300. The drip monitoring method 300 includes the following steps. It should be understood that the steps mentioned in this embodiment can be adjusted according to actual needs, and can be executed simultaneously.

In step 301, an initial monitoring signal is received. In one embodiment, the initial monitoring signal is generated by the user touching a physical or virtual button included in an operating interface of the drip monitoring system 100 to control the processing element 108 to start a monitoring process.

In step 302, the current carrying weight and motion data are weighed. In one embodiment, the processing element 108 controls the weighing device 102 to weigh the current carrying weight and motion data. For example, when a drip bag 1024 (or drip bottle) containing drip liquid is hung on the weighing device 102, the weight of the drip bag 1024 (or drip bottle) is weighed. Moreover, the current motion data of the weighing device 102 is weighed. The motion data is used to determine the real-time status of the drip bag 1024 (or drip bottle).

In step 303, whether the carrying weight is less than an alarm weight or not is determined. In one embodiment, the processing element 108 determines whether the weight of the drip bag 1024 (or drip bottle) is less than an alarm weight according to the carrying weight weighed by the weighing device 102. In one embodiment, when the drip in the drip bag 1024 (or the drip bottle) is continuously output, the carrying weight weighed by the weighing device 102 will continue to decrease. Therefore, an alarm weight is set to determine whether the drip in the drip bag 1024 (or the drip bottle) has reached the lower limit. In one embodiment, the alarm weight is the weight of the drip bag 1024 (or drip bottle) plus the empty drip tube and the lower limit dripping liquid. The value of the alarm weight can be stored in the storage element 104. The processing element 108 retrieves the alarm weight to perform the above-mentioned determination. When the carrying weight is not less than the alarm weight, step 304 is executed to continue the monitoring state. In step 305, after waiting for an interval, the processing element 108 monitors whether the current carrying weight weighed by the weighing device 102 is less than the alarm weight or not again.

In contrast, when the carrying weight is less than the alarm weight, step 306 is executed to determine whether the carrying weight is less than an empty weight or not. In one embodiment, the empty weight is the weight that there is no drip bag 1024 (or drip bottle) hung on the weighing device 102. Even though the drip bag 1024 (or drip bottle) does not be hung on the weighing device 102, the weighing device 102 could weigh not zero carrying weight due to the deformation caused by hanging the drip bag 1024 (or drip bottle) for a long time. Therefore, an empty weight is set to compensate the deformation. The empty weight is usually set to be greater than zero. Accordingly, when the carrying weight is less than the empty weight, the processing element 108 will still determine that the weighing device 102 is in the empty state. In an embodiment, the value of the empty weight is stored in the storage element 104. The processing element 108 accesses the empty weight from the storage element 104 to perform the above-mentioned determination process.

In step 306, when the current carrying weight is not less than the empty weight, the processing element 108 will determine that the weighing device 102 is not in the empty state. That is, a drip bag 1024 (or drip bottle)_is still hung on the weighing device 102. Because the carrying weight is less than the alarm weight but greater than the empty weight, in step 307, an alarm signal is issued. In one embodiment, the processing element 108 controls the alarm element 106 to issue the alarm signal to notify the medical staff to replace the drip bottle or drip bag.

In step 306, when the current carrying weight is less than the empty weight, that is, no drip bag 1024 (or drip bottle)_is hung on the weighing device 102. Therefore, in step 308, the processing element 108 will determine that the weighing device 102 is in an empty state. At this time, a return to zero calibration process of the weighing device 102 is performed.

For preventing the weighing device 102 from executing the calibration process in an abnormal state, before the weighing device 102 performs the return to zero calibration process, a determination step is performed to determine whether the weighing device 102 can perform the calibration process or not in step 309. That is, it is determined whether the motion data of the weighing device 102 is in the set calibration orientation. In one embodiment, the set calibration orientation is the orientation of the hook 1023 of the weighing device 102 perpendicular to the ground.

In one embodiment, the gravity sensor 1021 in the weighing device 102 senses the motion data of the weighing device 102. The processing element 108 reads the motion data sensed by the gravity sensor 1021 to determine whether the motion data is within this set calibration orientation. If the motion data is within this set calibration orientation, the processing element 108 performs a return to zero calibration process of the weighing device 102 in step 310. In contrast, if the motion data is not within this set calibration orientation, that is, the hook 1023 is not perpendicular to the ground, the processing element 108 prohibits the weighing device 102 from performing a return to zero calibration process and informs the relevant personnel. In step 305, an interval is waited. Then, the processing element 108 monitors whether the current carrying weight weighed by the weighing device 102 is less than an alarm weight again.

Figure 4:
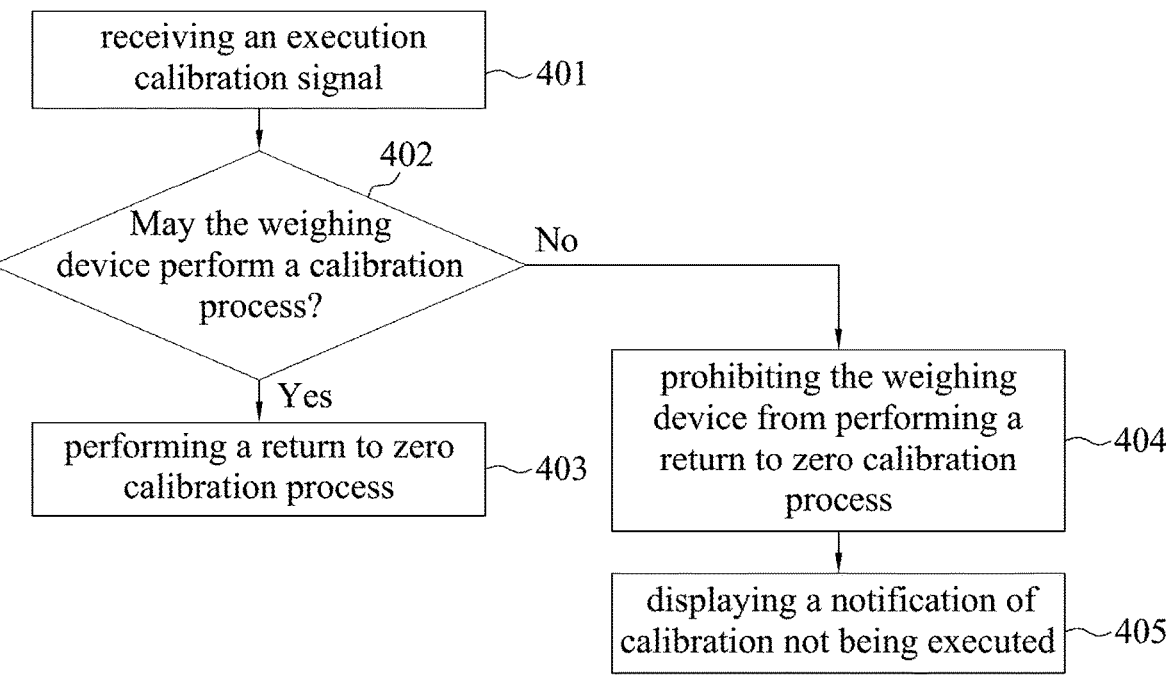
FIG. 4 is a flowchart of manual calibration process according to an embodiment of the present application.

FIG. 4 is a flowchart of manual calibration process according to an embodiment of the present application. Please refer to FIG. 1 and FIG. 4. In the manual calibration process 400, an execution calibration signal is received in step 401. In one embodiment, the execution calibration signal can be generated by the user touching a physical or virtual button included in an operating interface of the drip monitoring system 100 to control the processing element 108 to start a calibration process.

For preventing the weighing device 102 from executing the calibration process in an abnormal state, before the weighing device 102 performs the return to zero calibration process, a determination step is performed to determine whether the weighing device 102 can perform the calibration process or not in step 402. That is, it is determined whether the motion data of the weighing device 102 is in the set calibration orientation. In one embodiment, the set calibration orientation is the orientation of the hook 1023 of the weighing device 102 perpendicular to the ground. The processing element 108 reads the motion data sensed by the gravity sensor 1021 to determine whether the motion data is within this set calibration orientation. If the motion data is within this set calibration orientation, the processing element 108 performs a return to zero calibration process of the weighing device 102 in step 403. In contrast, if the motion data is not within this set calibration orientation, that is, the hook 1023 is not perpendicular to the ground, the processing element 108 prohibits the weighing device 102 from performing a return to zero calibration process in step 404. In step 405, a notification of calibration not being executed is displayed. In an embodiment, the display is performed through a display interface 109 of the drip monitoring system 100.

Figure 5:
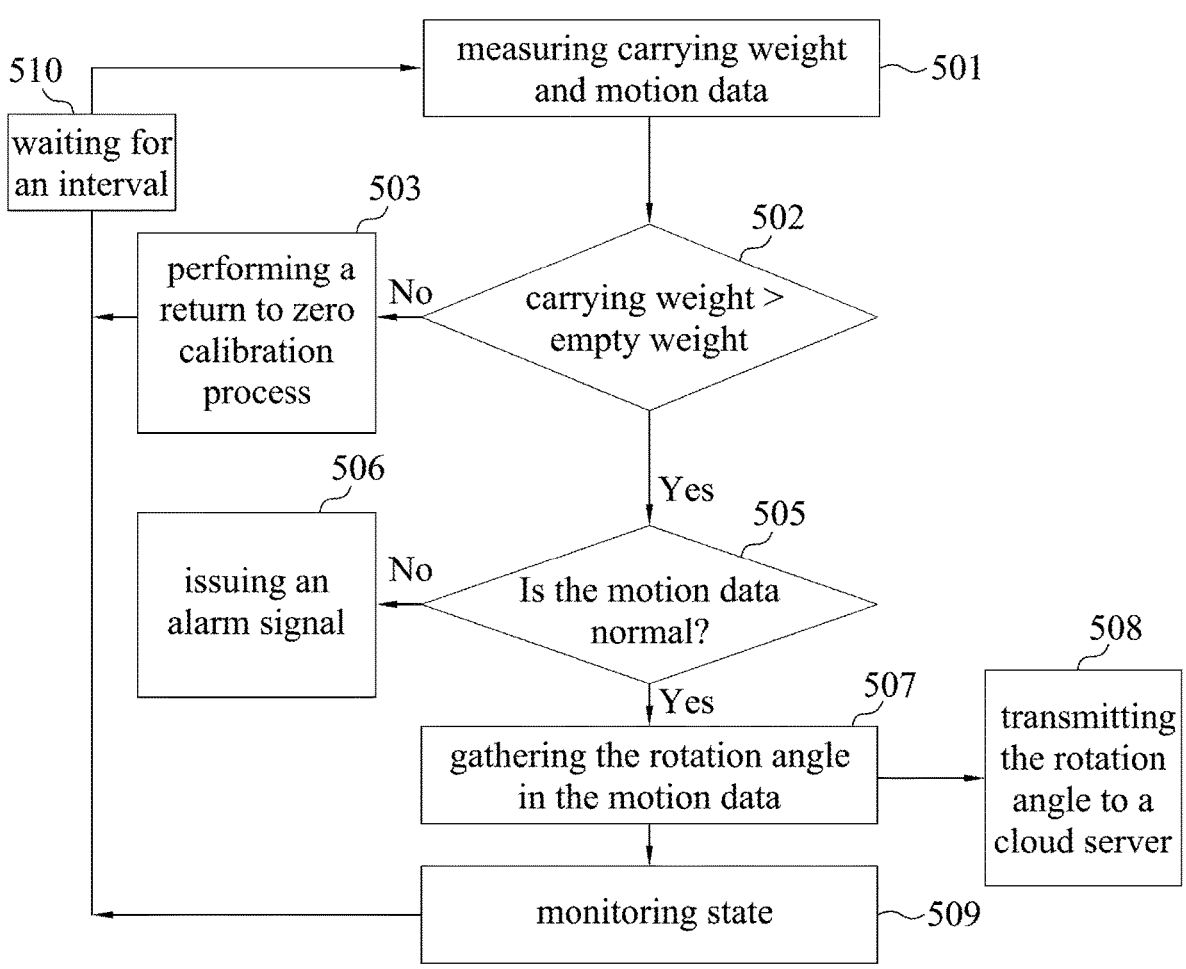
FIG. 5 is a flowchart of a method for locating and monitoring the instant status of the drip bottle or the drip bag according to an embodiment of the present application.

FIG. 5 is a flowchart of a method for locating and monitoring the instant status of the drip bottle or the drip bag 1024 according to an embodiment of the present application. Please refer to FIG. 1 and FIG. 5. It is noticed that the instant status of the drip bottle or drip bag 1024 will be continuously monitored before the weighing device 102 performs a return to zero calibration process.

The method 500 is to locate and monitor the instant status 500 of the drip bottle or drip bag. In step 501, the current carrying weight and the motion data is weighed. In one embodiment, the processing element 108 controls the weighing device 102 to weigh the current carrying weight and the motion data of the weighing device 102. For example, when a drip bag 1024 (or drip bottle) containing drip liquid is hung on the weighing device 102, the weight of the drip bag 1024 (or drip bottle) is weighed, and the current motion data of the weighing device 102 is detected. The motion data is used to determine the instant status of the drip bag 1024 (or drip bottle). In step 502, a determination step is performed to determine whether the carrying weight is greater than the empty weight. When the current carrying weight is less than the empty weight, that is, no drip bag 1024 (or drip bottle) is hung on the weighing device 102, the processing element 108 will determine that the weighing device 102 is in an empty state. Therefore, in step 503, the return to zero calibration process of the weighing device 102 is performed Then, in step 505, a determination step is performed to determine whether or not the motion data is normal. In one embodiment, the processing element 108 gathers the motion data detected by the gravity sensor 1021 in the weighing device 102. The positioning element 1022 broadcasts the identification code and the motion data through a Bluetooth signal. When the signal receiver 200 within the communication range receives the Bluetooth signal, the position of the weighing device 102 may be determined through the identification code and the motion data value therein.

In one embodiment, the acceleration changes, such as the X axis, the Y axis, and the Z axis, of the motion data sensed by the gravity sensor 1021 in a short period of time are calculated to determine the instant status of the drip bottle or drip bag 1024. If the motion data is abnormal in step 505, a warning message is generated in step 506. In one embodiment, a warning message of abnormal condition of the drip bottle or drip bag 1024 is generated. In one embodiment, the situation of the drip bottle or drip bag 1024 falling may cause the acceleration data in the X-axis, the Y-axis, and the Z-axis change instantaneously. When the change exceeds a set threshold, a warning message of abnormal condition of the drip bottle or drip bag 1024 is generated in step 506. In contrast, if the motion data is normal in step 505, the processing element 108 gathers the rotation angle in the motion data in step 507. In one embodiment, if the change does not exceed the set threshold, the drip bottle or drip bag 1024 is in a normal use state is determined. Then, the processing element 108 gathers the rotation angle in the motion data in step 507 and sends the rotation angle to the cloud server 210 in step 508. In one embodiment, the cloud server 210 can indirectly determine the traveling direction and position of the patient or the weighing device 102 based on the rotation angle.

In step 509, the monitoring state is performed is performed. In step 510, after an interval time, the processing element 108 gathers the carrying weight weighed by the weighing device 102 again.

Accordingly, a gravity sensor is installed on the weighing device to sense the motion data of the weighing device. The motion data is used to determine the current orientation of the weighing device. The current orientation is used to determine whether to perform a return to zero calibration process. Accordingly, the shortcomings of performing the return to zero calibration process by the weighing device in an abnormal orientation are eliminated. Furthermore, it is possible to locate and determine whether an unexpected situation has occurred based on the real-time motion data and the amount of change.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A drip monitoring system, comprising:
   a processing element;
   a weighing device coupled to the processing element, wherein the weighing device has a hook to hang a drip bag or a drip bottle and a gravity sensor to sense a motion data of the weighing device, wherein the weighing device is configured to weigh a weight of the drip bag or the drip bottle hanged in the hook; and
   an alarm element configured to generate an alarm message according to a control signal from the processing element;
   wherein the processing element gathers the motion data of the weighing device when the weight of the drip bag or the drip bottle is less than an empty weight, and
   the processing element determines, based on the motion data, whether the weighing device is in an identified calibration orientation, wherein the weighing device in the identified calibration orientation indicates that the hook of the weighing device is perpendicular to ground, and the weighing device not in the identified calibration orientation indicates that the hook of the weighing device is not perpendicular to the ground,
   when the processing element determines, based on the motion data, that the weighing device is in the identified calibration orientation, the processing element performs a zeroing calibration process of the weighing device.

2. The drip monitoring system of claim 1, wherein when the weight of the drip bag or the drip bottle is larger than an alarm weight, the processing element gathers the weight of the drip bag or the drip bottle to compare with the alarm weight again after an interval.

3. The drip monitoring system of claim 1, wherein the weighing device further comprises a positioning element configured to broadcast an identification code and the motion data through a wireless signal, wherein a server determines a location of the weighing device according to the identification code and the motion data.

4. The drip monitoring system of claim 1, further comprising a communication element coupled to the processing element.

5. The drip monitoring system of claim 1, wherein when the processing element determines the hook of the weighing device is not in the identified calibration orientation based on the motion data, the processing element does not perform the zeroing calibration process of the weighing device.

6. The drip monitoring system of claim 1, wherein the processing element gathers the weight of the drip bag or the drip bottle to compare with an alarm weight,
   wherein the processing element compares the weight of the drip bag or the drip bottle with the empty weight when the weight of the drip bag or the drip bottle is less than the alarm weight, wherein the empty weight is less than the alarm weight, and wherein when the weight of the drip bag or the drip bottle is less than the alarm weight but greater than the empty weight, the processing element generate the control signal to control the alarm element to generate the alarm message.

7. The drip monitoring system of claim 1, wherein the processing element gathers the motion data to calculate a change of the motion data in a time period.

8. The drip monitoring system of claim 7, wherein when the change of the motion data in the time period is larger than a threshold, the processing element controls the alarm element to generate the alarm message.

9. The drip monitoring system of claim 8, wherein when the change of the motion data in the time period is less than the threshold, the processing element transmits the motion data to a server, and the server determines a travel direction of the weighing device according to the motion data.

10. A drip monitoring method, comprising:

weighing a weight of a drip bag or a drip bottle hanged in a hook by a weighing device, wherein the weighing device has a gravity sensor to sense a motion data of the weighing device and the hook perpendicular to ground to hang the drip bag or the drip bottle;

gathering the motion data of the weighing device by a processing element when the weight of the drip bag or the drip bottle is less than an empty weight;

determining whether the weighing device is in an identified calibration orientation by the processing element based on the motion data, wherein the weighing device in the identified calibration orientation indicates that the hook of the weighing device is perpendicular to ground, and the weighing device not in the identified calibration orientation indicates that the hook of the weighing device is not perpendicular to the ground; and performing a zeroing calibration process by the processing element of the weighing device when the processing element determines the hook of the weighing device is in the identified calibration orientation.

11. The drip monitoring method of claim 10, wherein when the weight of the drip bag or the drip bottle is larger than an alarm weight, the processing element gathers the weight of the drip bag or the drip bottle to compare with the alarm weight again after an interval.

12. The drip monitoring method of claim 10, further comprising a communication element coupled with the processing element.

13. The drip monitoring method of claim 10, wherein when the processing element determines the weighing device is not in the identified calibration orientation based on the motion data, the processing element does not perform the zeroing calibration process of the weighing device.

14. The drip monitoring method of claim 10, wherein the processing element gathers the motion data to calculate a change of the motion data in a time period.

15. The drip monitoring method of claim 14, wherein when the change of the motion data in the time period is larger than a threshold, the processing element controls an alarm element to generate an alarm message.

16. The drip monitoring method of claim 15, wherein when the change of the motion data in the time period is less than the threshold, the processing element transmits the motion data to a server, and the server determines a travel direction of the weighing device according to the motion data.

17. The drip monitoring method of claim 10, wherein the weighing device further comprises a positioning element configured to broadcast an identification code and the motion data through a wireless signal, wherein a server determines a location of the weighing device according to the identification code and the motion data.

18. The drip monitoring method of claim 10, further comprising:

gathering the weight of the drip bag or the drip bottle to compare with an alarm weight by the processing element coupling with the weighing device; and comparing the weight of the drip bag or the drip bottle with the empty weight by the processing element when the weight of the drip bag or the drip bottle is less than the alarm weight, wherein the empty weight is less than the alarm weight;

wherein when the weight of the drip bag or the drip bottle is less than the alarm weight but greater than the empty weight, the processing element generate a control signal to control an alarm element to generate an alarm message.

* * * * *